US010662220B2

United States Patent
Liu et al.

(10) Patent No.: US 10,662,220 B2
(45) Date of Patent: May 26, 2020

(54) SYNTHESIS AND COMPOSITION OF RAPAFUCIN LIBRARIES

(71) Applicant: The Johns Hopkins University, Baltimore, MD (US)

(72) Inventors: Jun Liu, Baltimore, MD (US); Jingxin Wang, Baltimore, MD (US); Zufeng Guo, Baltimore, MD (US); Sam Hong, Baltimore, MD (US); Wukun Liu, Baltimore, MD (US); Hanjing Peng, Baltimore, MD (US); Manisha Das, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/074,017

(22) PCT Filed: Feb. 3, 2017

(86) PCT No.: PCT/US2017/016481
§ 371 (c)(1),
(2) Date: Jul. 30, 2018

(87) PCT Pub. No.: WO2017/136708
PCT Pub. Date: Aug. 10, 2017

(65) Prior Publication Data
US 2019/0092808 A1 Mar. 28, 2019

Related U.S. Application Data

(60) Provisional application No. 62/291,437, filed on Feb. 4, 2016.

(51) Int. Cl.
*C07K 1/04* (2006.01)
*C07K 17/08* (2006.01)
(Continued)

(52) U.S. Cl.
CPC .............. *C07K 1/047* (2013.01); *C07K 5/10* (2013.01); *C07K 17/08* (2013.01); *G01N 33/574* (2013.01);
(Continued)

(58) Field of Classification Search
CPC ..................................................... C07K 1/047
(Continued)

(56) References Cited

U.S. PATENT DOCUMENTS

| 5,527,907 A | 6/1996 | Or et al. |
| 5,798,355 A | 8/1998 | Steiner et al. |

(Continued)

FOREIGN PATENT DOCUMENTS

| WO | WO 1996/40140 A1 | 12/1996 |
| WO | WO 2010/004304 A1 | 1/2010 |

(Continued)

OTHER PUBLICATIONS

Chakraborty, T. K. et al.: "Design and Synthesis of a Rapamycin-Based High Affinity Binding FKBP12 Ligand", Chemistry & Biology, Mar. 1, 1995, vol. 2, pp. 157-161, XP002938574.
(Continued)

*Primary Examiner* — Taofiq A Solola
(74) *Attorney, Agent, or Firm* — DLA Piper LLP (US)

(57) ABSTRACT

A Rapafucin library containing compounds of the general structure, (A) and (E), and a synthesis of these compounds are provided.

5 Claims, 1 Drawing Sheet

(51) Int. Cl.
*G01N 33/574* (2006.01)
*C07K 5/10* (2006.01)
*G01N 33/68* (2006.01)
*B82Y 5/00* (2011.01)

(52) U.S. Cl.
CPC ............ *G01N 33/6803* (2013.01); *B82Y 5/00* (2013.01); *G01N 2500/00* (2013.01); *G01N 2570/00* (2013.01); *G01N 2800/24* (2013.01)

(58) Field of Classification Search
USPC ........................................................ 540/474
See application file for complete search history.

(56) References Cited

U.S. PATENT DOCUMENTS

| | | |
|---|---|---|
| 6,984,635 B1 | 1/2006 | Schreiber et al. |
| 7,056,935 B2 | 6/2006 | Steiner |
| 7,803,808 B2 | 9/2010 | Gregory |
| 9,250,237 B2 | 2/2016 | Liu et al. |
| 2002/0052410 A1 | 5/2002 | Steiner |
| 2008/0306098 A1 | 12/2008 | Mutz |
| 2009/0253732 A1 | 10/2009 | Gregory |
| 2014/0073581 A1 | 3/2014 | Liu et al. |
| 2015/0018340 A1 | 1/2015 | Gopalakrishnan |

FOREIGN PATENT DOCUMENTS

| | | |
|---|---|---|
| WO | WO 2012/075048 A2 | 6/2012 |
| WO | WO 2014/201405 A1 | 12/2014 |

OTHER PUBLICATIONS

Extended European Search Report dated Aug. 16, 2019, regarding EP 17 74 8264.

Upadhyaya, Punit et al.: "*Inhibition of Ras Signaling by Blocking Ras-Effector Interactions with Cyclic Peptides*"; Angew. Chem. Int Ed., Jun. 22, 2015, vol. 54, No. 26, pp. 7602-7606. XP055238762.

Wu, Xianghong et al.: "*Creating Diverse Target-Binding Surfaces on FKBP12: Synthesis and Evaluation of a Rapamycin Analogue Library*"; ACS Comb Sci, Sep. 12, 2011, vol. 13, No. 5, 28, pp. 486-495, XP55469664.

Wu, Xianghong et al.: "*Inhibition of Ras-effector interactions by cyclic peptides*": Med. Chem. Commun., Jan. 1, 2013, vol. 4, No. 2, pp. 378-382, XP55610945.

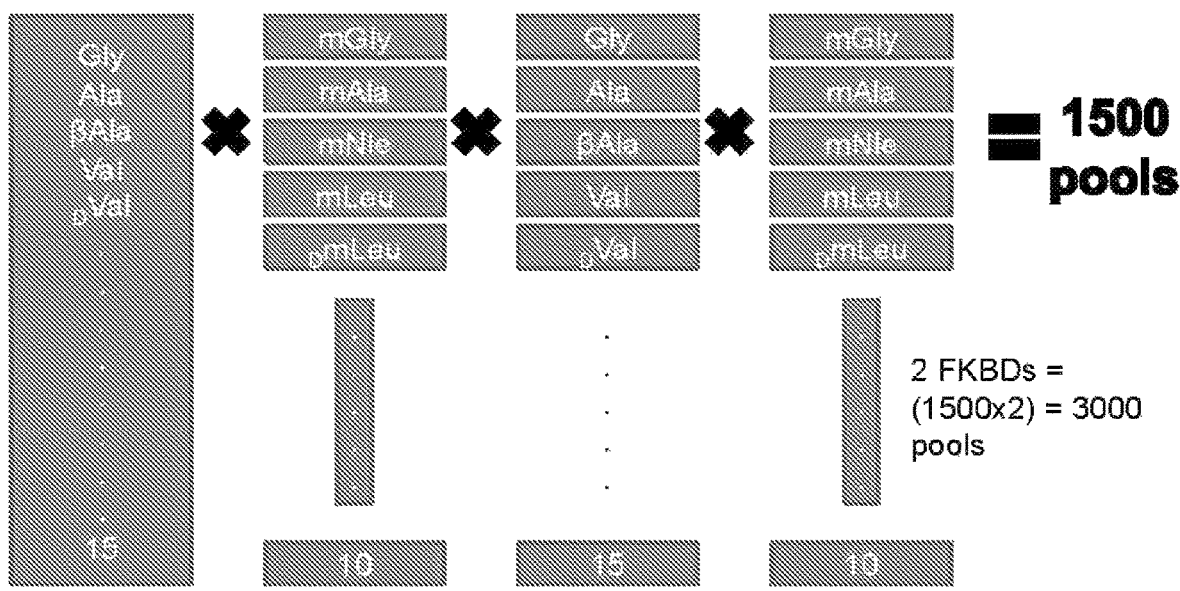

SYNTHESIS AND COMPOSITION OF RAPAFUCIN LIBRARIES

RELATED APPLICATIONS

This application is a 35 USC § 371 National Stage application of International Application No. PCT/US2017/016481 filed Feb. 3, 2017, now pending; which claims the benefit under 35 USC § 119(e) to U.S. application Ser. No. 62/291,437 filed Feb. 4, 2016. The disclosure of each of the prior applications is considered part of and is incorporated by reference in the disclosure of this application.

GRANT INFORMATION

This invention was made with government support under National Institutes of Health grant DP1CA174428. The government has certain rights in the invention.

BACKGROUND OF THE INVENTION

Field of the Invention

The invention relates generally to hybrid cyclic molecules, and more specifically to hybrid cyclic libraries based on the immunophilin ligand family of natural products FK506 and rapamycycin.

Background Information

The macrocyclic natural products FK506 and rapamycin are approved immunosuppressive drugs with important biological activities. Both have been shown to inhibit T cell activation, albeit with distinct mechanisms. In addition, rapamycin has been shown to have strong anti-proliferative activity. FK506 and rapamycin share an extraordinary mode of action; they act by recruiting an abundant and ubiquitously expressed cellular protein, the prolyl cis-trans isomerase FKBP, and the binary complexes subsequently bind to and allosterically inhibit their target proteins calcineurin and mTOR, respectively. Structurally, FK506 and rapamycin share a similar FKBP-binding domain but differ in their effector domains. In FK506 and rapamycin, nature has taught us that switching the effector domain of FK506 to that in rapamycin, it is possible to change the targets from calcineurin to mTOR. The generation of a rapafucin library of macrocytes that contain FK506 and rapamycin binding domains should have great potential as new leads for developing drugs to be used for treating diseases.

With the completion of the sequencing and annotation of the human genome, a complete catalog of all human proteins encoded in the genome is now available. The functions of a majority of these proteins, however, remain unknown. One way to elucidate the functions of these proteins is to find small molecule ligands that specifically bind to the proteins of interest and perturb their biochemical and cellular functions. Thus, a major challenge for chemical biologists today is to discover new small molecule probes for new proteins to facilitate the elucidation of their functions. The recent advance in the development of protein chips has mitered an exciting new opportunity to simultaneously screen chemical libraries against nearly the entire human proteome. A single chip, in the form of a glass slide, is sufficient to display an entire proteome in duplicate arrays. Recently, a protein chip with 17,000 human proteins displayed on a single slide has been produced. A major advantage of using human protein chips for screening is that the entire displayed proteome can be interrogated at once in a small volume of assay buffer (<3 mL). Screening of human protein chips, however, is not yet feasible with most, if not all, existing chemical libraries due to the lack of a universal readout for detecting the binding of a ligand to a protein on these chips. While it is possible to add artificial tags to individual compounds in a synthetic library, often the added tags themselves interfere with the activity of ligands. Thus, there remains a need for new compounds and methods for screening chemical libraries against the human proteome.

SUMMARY OF THE INVENTION

One embodiment of the present invention is to provide a compound of the following structure:

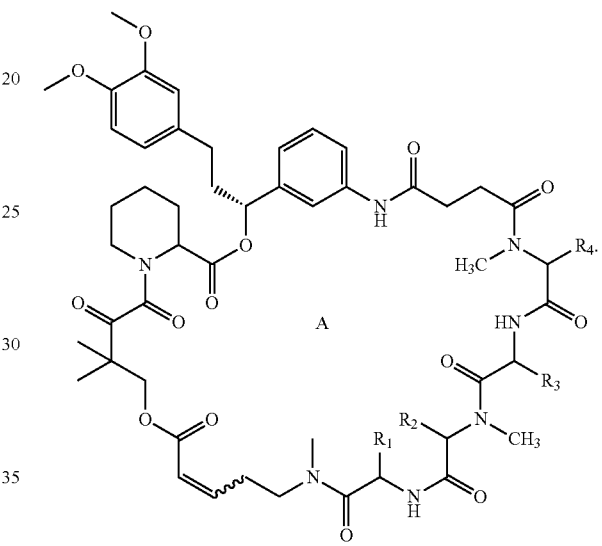

$R_1$ and $R_3$ can independently be any of the following compounds:

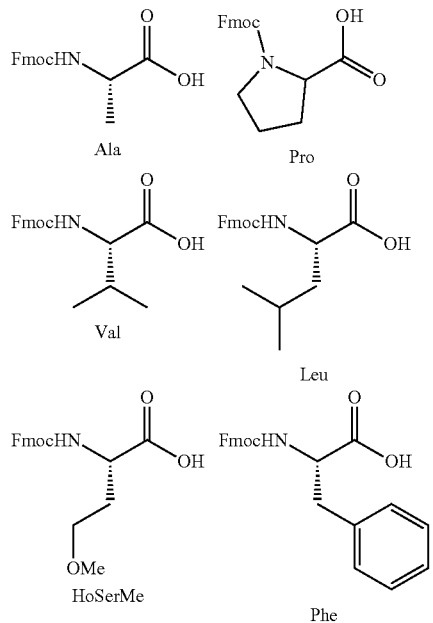

-continued
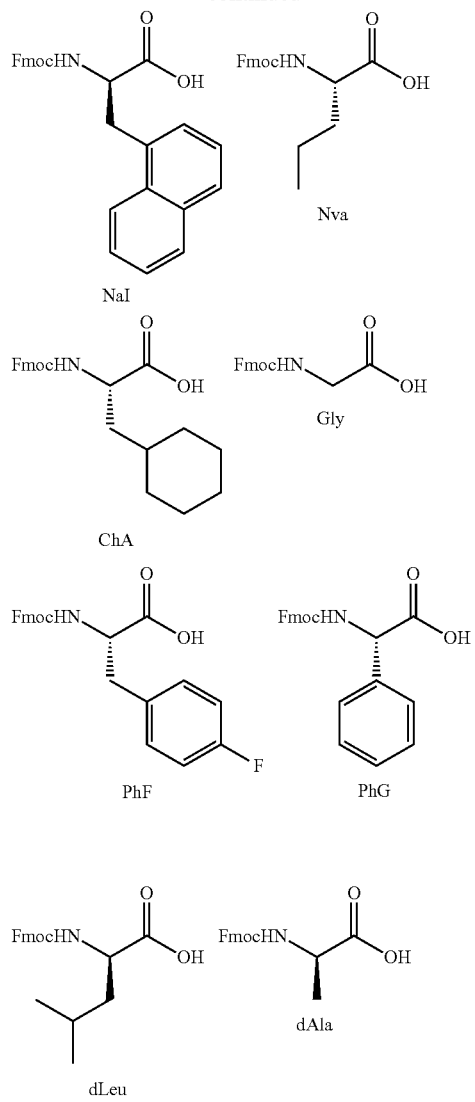
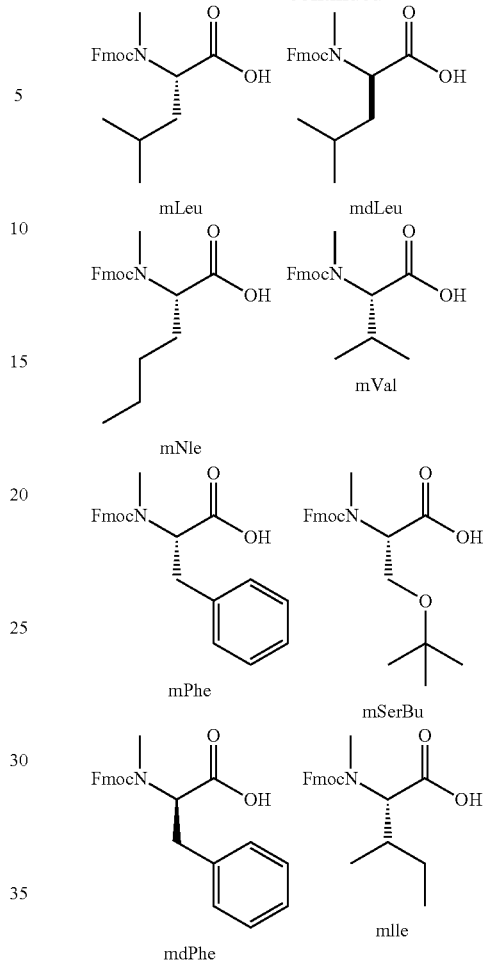
$R_2$ and $R_4$ can independently be any of the following compounds:
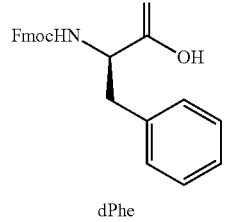
Another embodiment of the present invention is to provide a compound of the following structure:
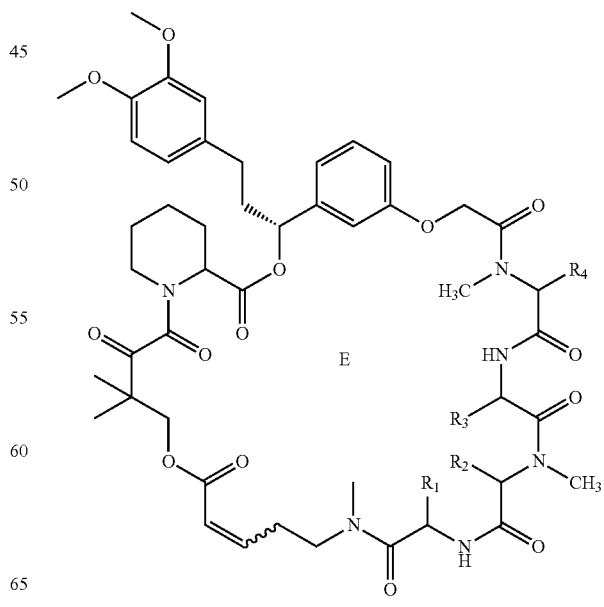

$R_1$, $R_2$, $R_3$ and $R_4$ are selected from the same groupings of compounds listed above.

Another embodiment of the present invention is to provide a compound that includes A15-34-2, A15-39-1, A15-39-2, A15-39-4, A15-39-6, A15-39-8, A15-39-15, A15-40-2, A15-40-4, A15-40-15, E15-32-2, E15-33-1, E15-33-2, E15-34-1, E15-34-2, E15-39-1, E15-39-2, E15-39-5, E15-40-2, E15-40-4, E15-S-19, E15-S-21, and E15-S-22.

Another embodiment of the present invention is to provide synthetic methods as outlined in the "Detailed Description of the Invention" for producing a Rapafucin library.

BRIEF DESCRIPTION OF THE DRAWINGS

FIG. 1. Number of compounds in library.

DETAILED DESCRIPTION OF THE INVENTION

Example 1

Scheme 1- Synthetic scheme for Rapafucin molecules containing amide mFKBD and ether mFKBD.

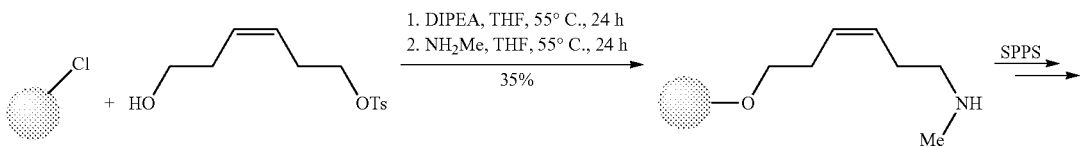

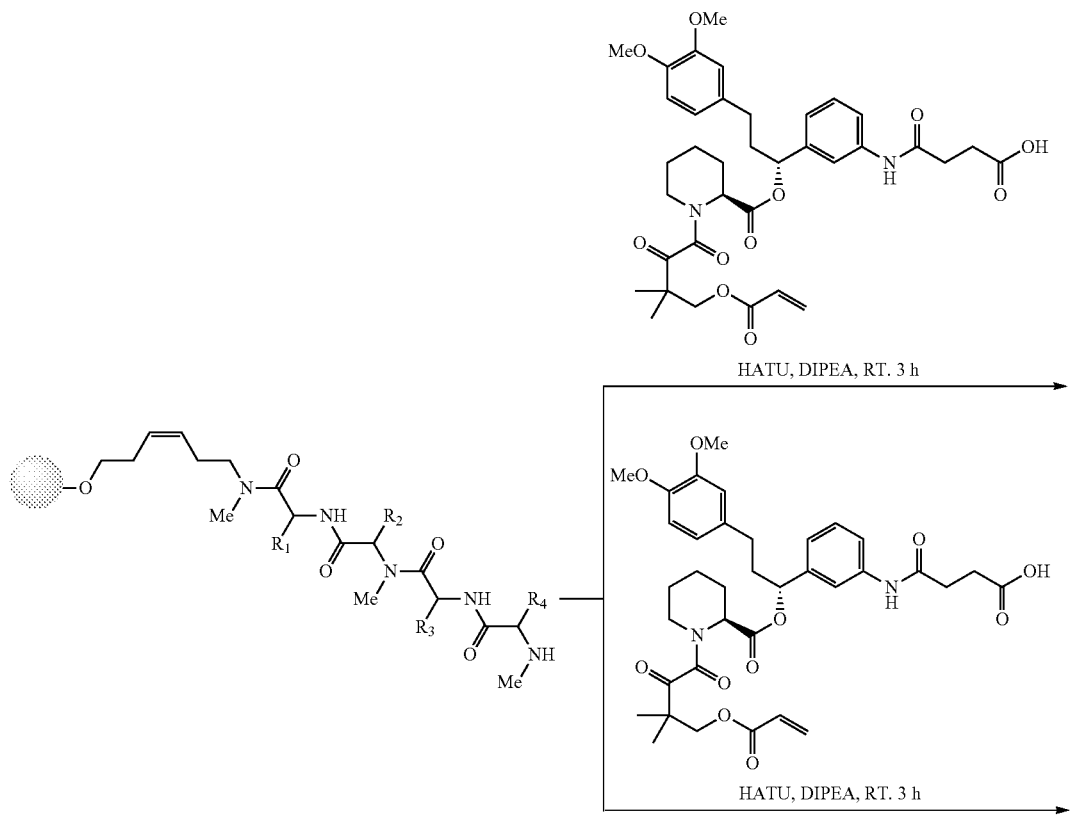

-continued
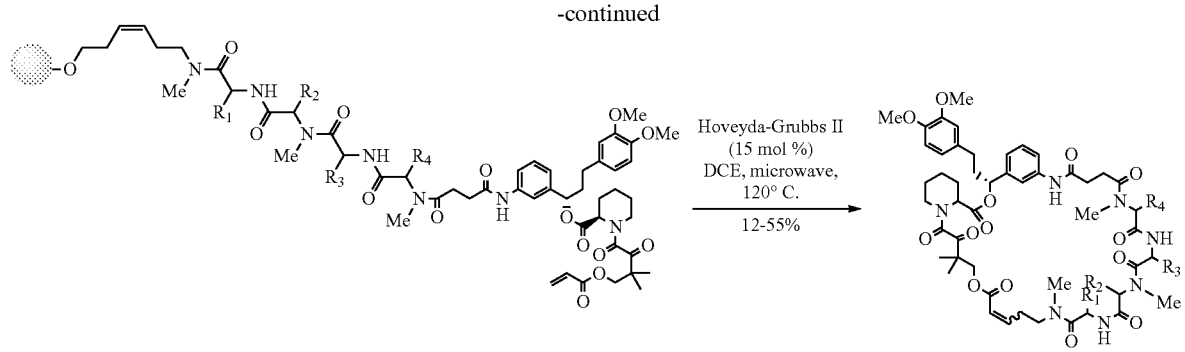
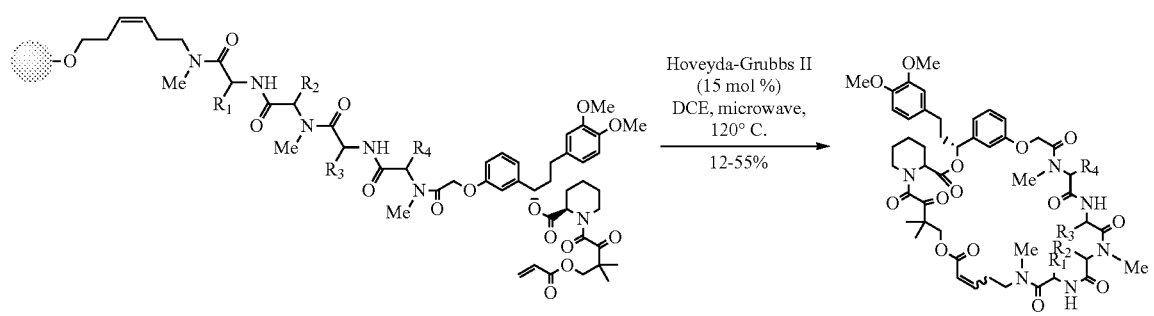
$R_1$ and $R_3$ in Scheme 1 are amino acids selected from the following group of amino acids:
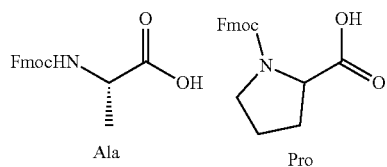
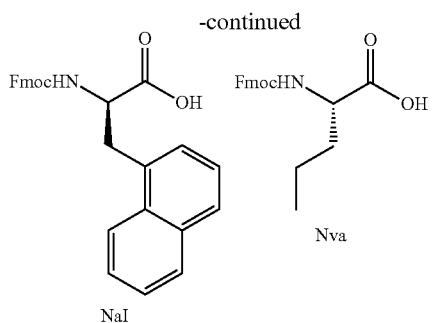
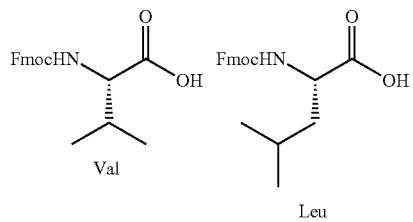
-continued
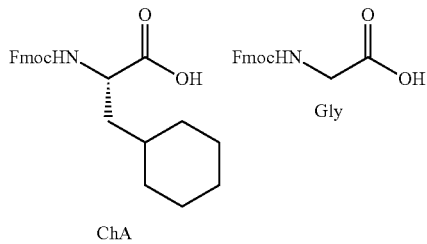
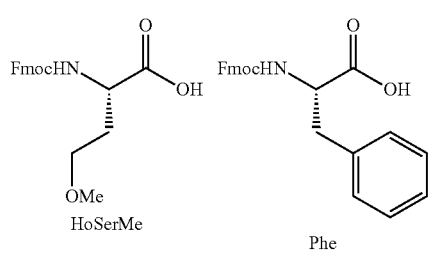
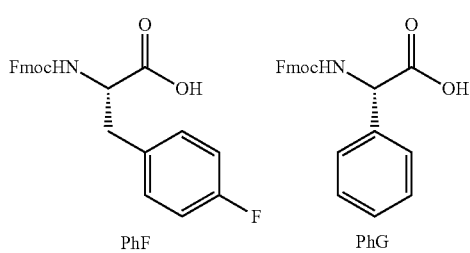

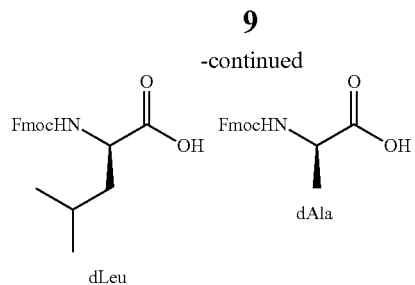
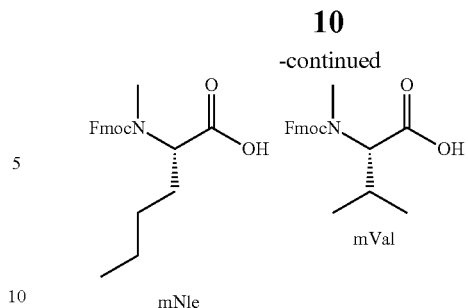
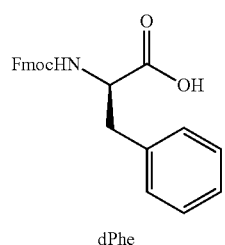
R₂ and R₄ in Scheme 1 are amino acids selected from the following group of amino acids:
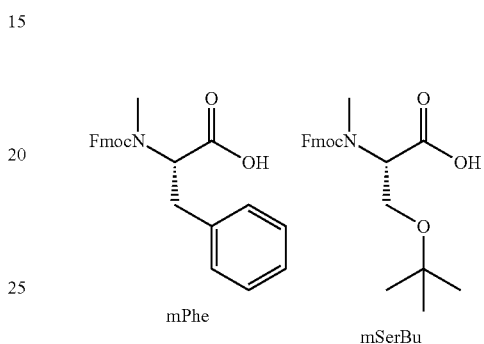
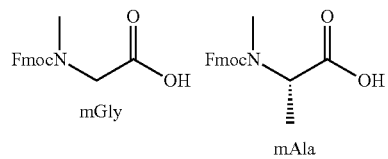
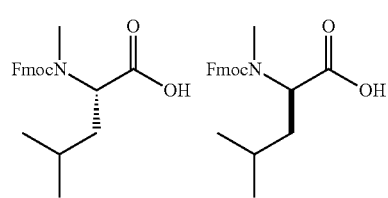
The synthesis of the amide mFKBD in Scheme 1 is as follows:
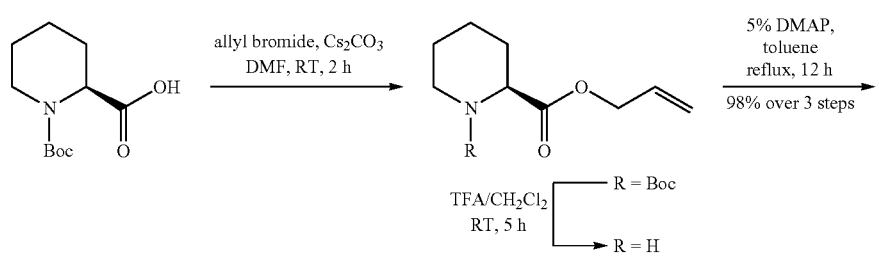

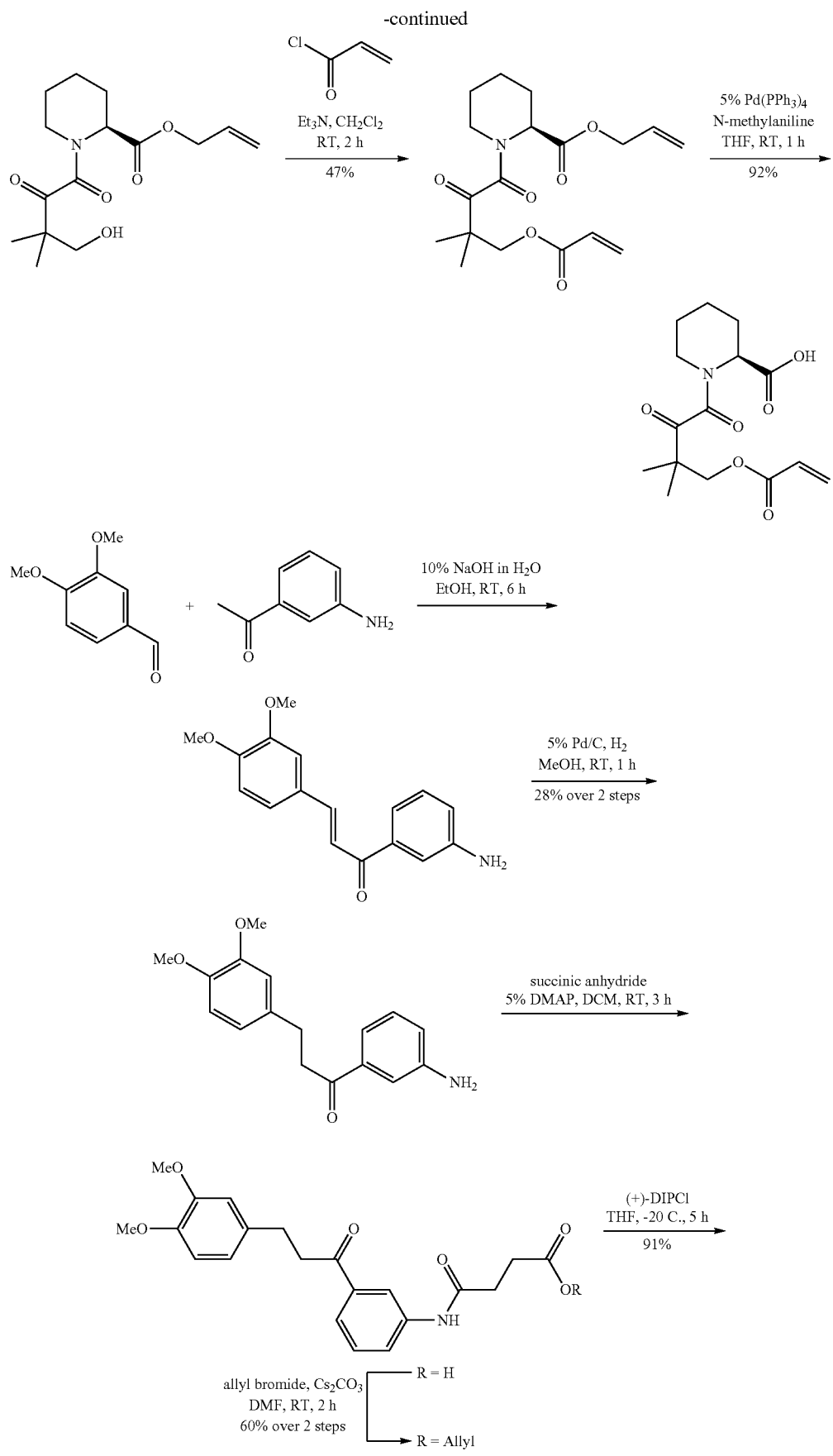

-continued
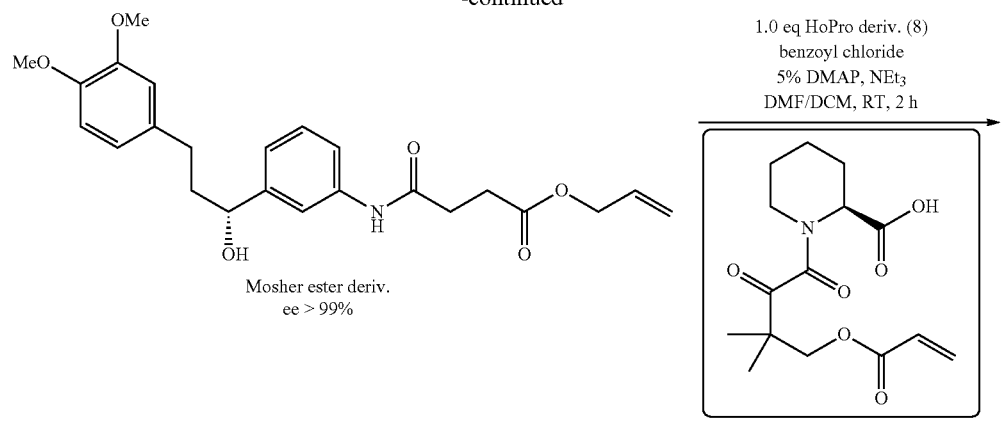
Mosher ester deriv.
ee > 99%
1.0 eq HoPro deriv. (8)
benzoyl chloride
5% DMAP, NEt₃
DMF/DCM, RT, 2 h
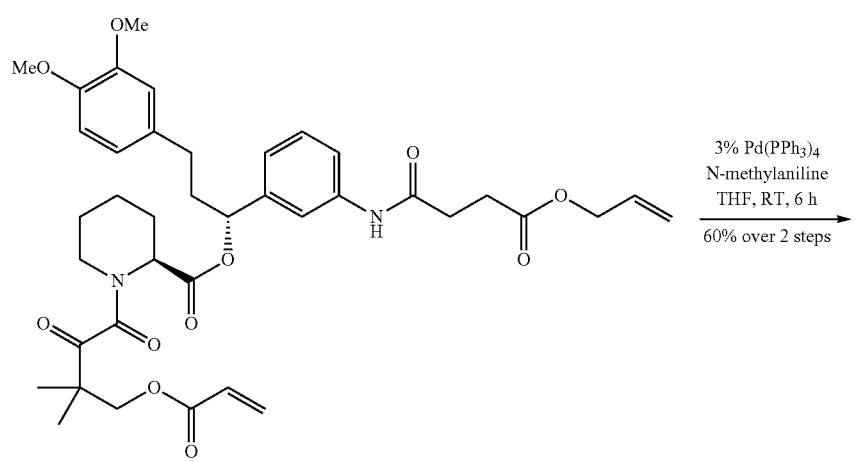
3% Pd(PPh₃)₄
N-methylaniline
THF, RT, 6 h
60% over 2 steps
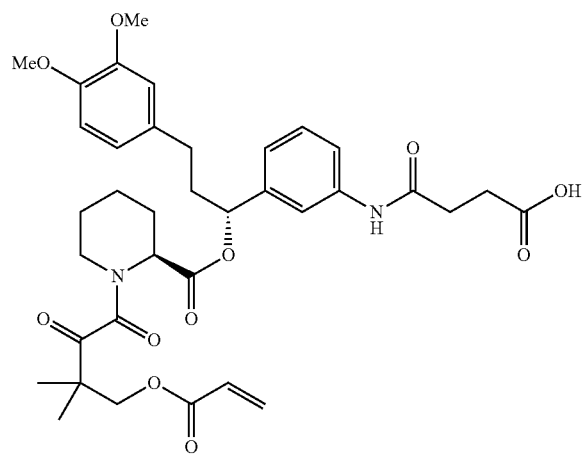

The synthesis of the ether mFKBD in Scheme 1 is as follows:
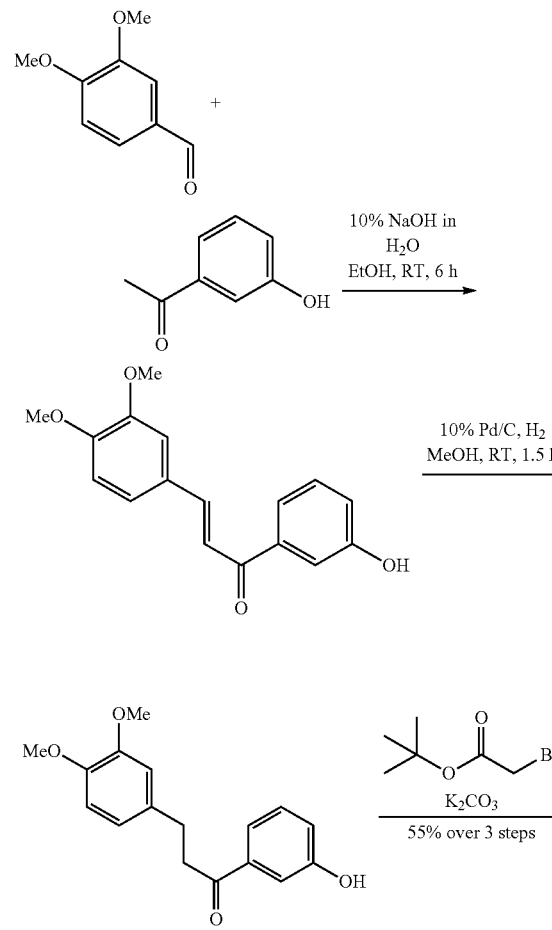
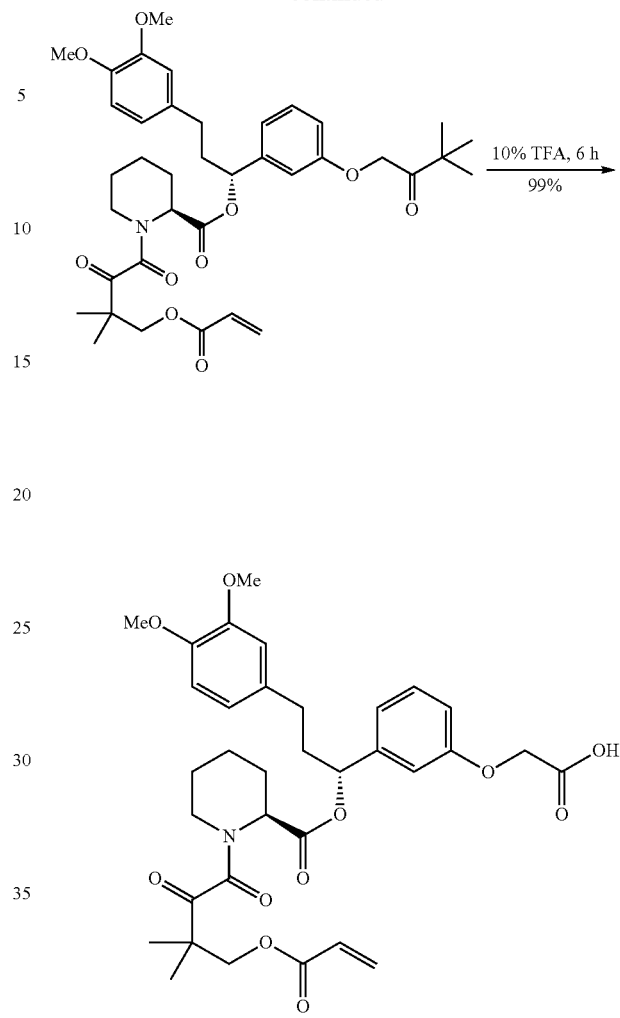
The general formula for a Rapafucin with an amide mFKBD is represented by "A".
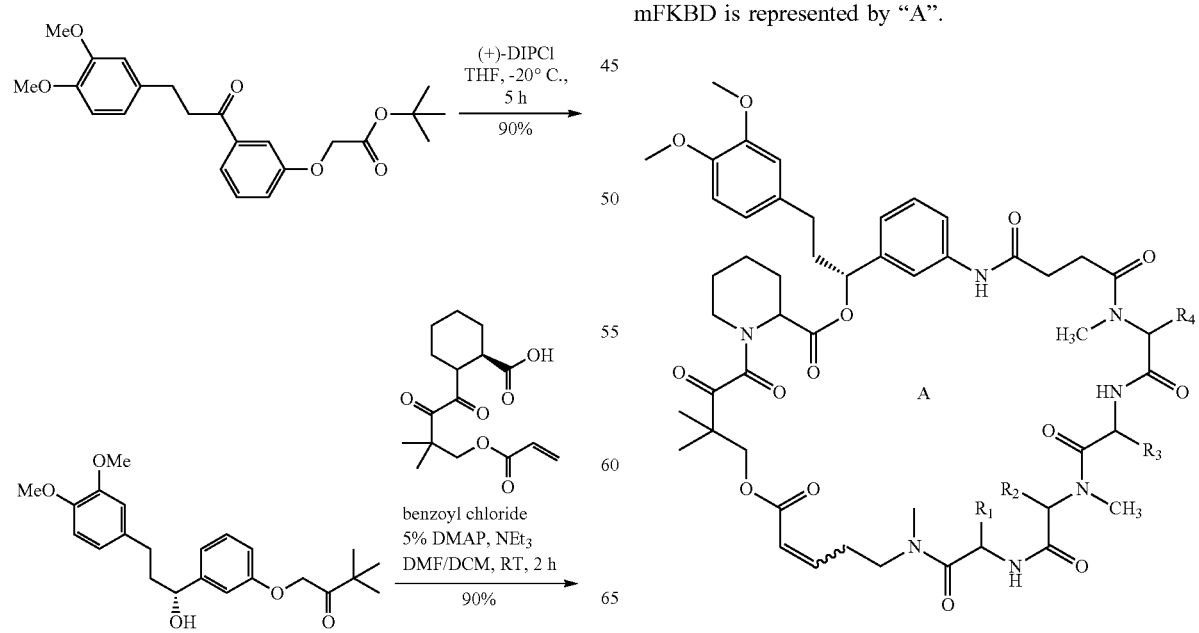

The general formula for a Rapafucin with an ether mFKBD is represented by "E".

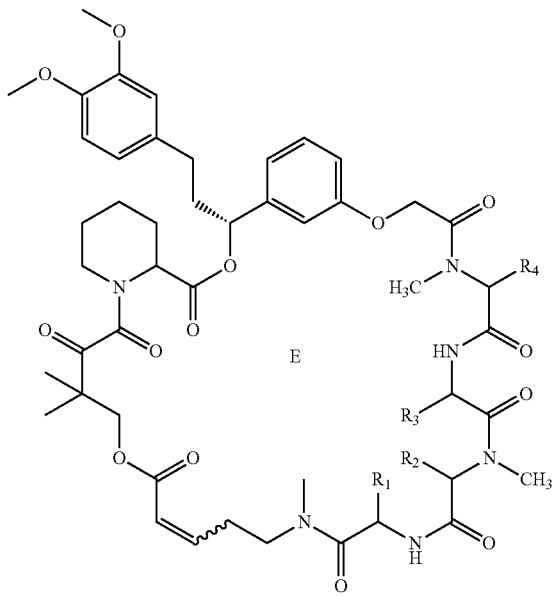

E

Specific Examples of "A" and "E" as well as their properties are listed in Table 1.

Approximately, 45,000 compounds were obtained as part of the Rapafucin library (FIG. 1).

Although the invention has been described with reference to the above example, it will be understood that modifications and variations are encompassed within the spirit and scope of the invention. Accordingly, the invention is limited only by the following claims.

REFERENCES

The following reference is relied upon and incorporated herein in its entirety.

1. US 2014/0073581.

What is claimed is:
1. A compound of Formula I:

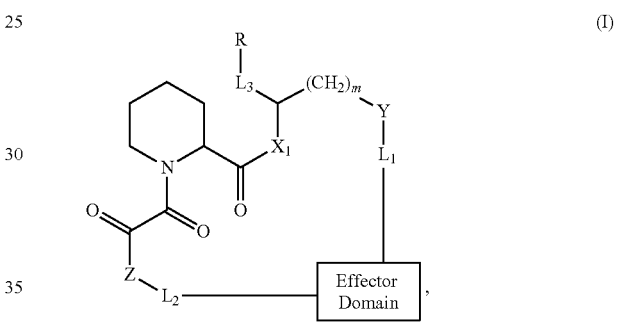

(I)

TABLE 1

| Name | Sequence | Hillslope | IC50(nM) | Name | Sequence | Hillslope | IC50(nM) |
|---|---|---|---|---|---|---|---|
| A15-39-1 | Gly-dmPhe-Pro-mVal | −0.9753 | 27.95 | E15-40-2 | Ala-dmPhe-Pro-mIle | −1.212 | 34.15 |
| A15-39-2 | Ala-dmPhe-Pro-mVal | −1.164 | 23.73 | E15-40-4 | Nva-dmPhe-Pro-mIle | −1.195 | 173.1 |
| A15-39-4 | Nva-dmPhe-Pro-mVal | −1.112 | 18 | E15-32-2 | Ala-dmPhe-Pro-mAla | −1.134 | 66.71 |
| A15-39-6 | Leu-dmPhe-Pro-mVal | −1.105 | 54.14 | E15-33-1 | Gly-dmPhe-Pro-mNle | −1.007 | 13.91 |
| A15-39-8 | Phe-dmPhe-Pro-mVal | −1.191 | 54.99 | E15-33-2 | Ala-dmPhe-Pro-mNle | −1.017 | 9.76 |
| A15-39-15 | Phg-dmPhe-Pro-mVal | −0.8952 | 16.51 | E15-34-1 | Gly-dmPhe-Pro-mLeu | −1.494 | 28.54 |
| E15-39-1 | Gly-dmPhe-Pro-mVal | −1.024 | 48.88 | E15-34-2 | Ala-dmPhe-Pro-mLeu | −0.741 | 10.53 |
| E15-39-2 | Ala-dmPhe-Pro-mVal | −1.125 | 33.54 | A15-34-2 ** | Ala-dmPhe-Pro-mLeu | −0.3876 | 31.45 |
| E15-39-5 | HoSMe-dmPhe-Pro-mVal | −0.8614 | 59.46 | E15-S-19 | Gly-dmPhe-Pro-mNva | −1.363 | 42.27 |
| A15-40-2 | Ala-dmPhe-Pro-mIle | −0.6276 | 34.4 | E15-S-21 | Gly-dmPhe-Pro-dmAla | −1.314 | 154.9 |
| A15-40-4 | Nva-dmPhe-Pro-mIle | −0.87 | 12.19 | E15-S-22 | Gly-dmPhe-Pro-Ach | −1.236 | 261.9 |
| A15-40-15 | Phg-dmPhe-Pro-mIle | −0.9138 | 100.1 | | | | | or a pharmaceutically acceptable salt thereof, wherein:
R is

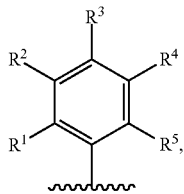

$R^1$, $R^4$, and $R^5$ are each hydrogen, $R^2$ and $R^3$ are each methoxy;
m=0:
$X_1$ is O or $NR^6$;
Y is

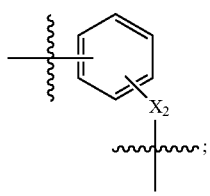

$X_2$ is O or $NR^6C(O)$;
$R^6$ is hydrogen or alkyl;
Z is

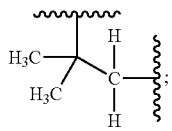

$L_1$ is —$CH_2$—C(O)— or —$(CH_2)_2$C(O)—;
$L_2$ is —OCO—CH=CH—$(CH_2)_2$N(Me)-;
$L_3$ is —$CH_2CH_2$—; and
the effector domain has the structure of formula (VIII)

$$-AA_1-AA_2-AA_3-AA_4-  \qquad (VIII)$$

wherein $AA_1$, $AA_2$, $AA_3$ and $AA_4$ are each independently selected from

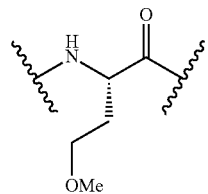
HoSerMe ,

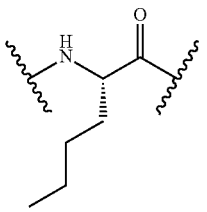
,

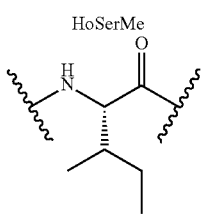
,

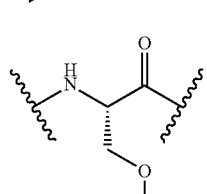
,

-continued

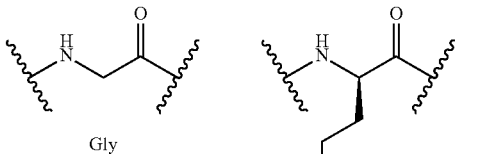
Gly ,

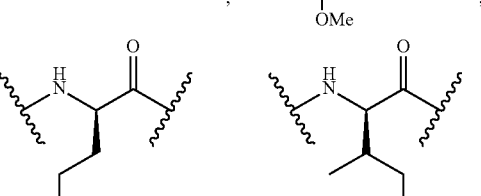
OMe ,

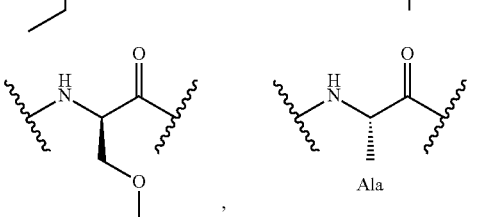
,

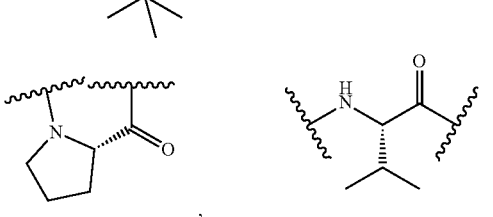
,

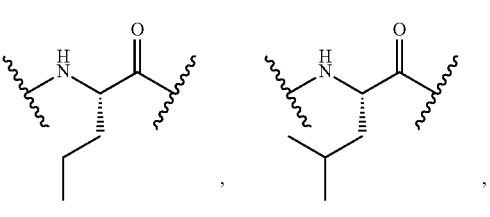
,
Ala ,

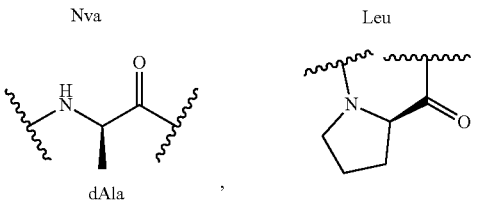
Pro ,
Val ,

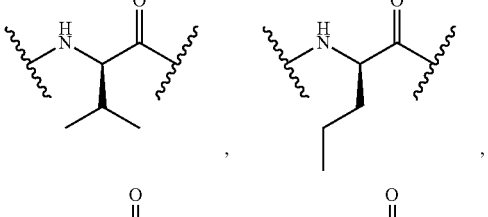
Nva ,
Leu ,

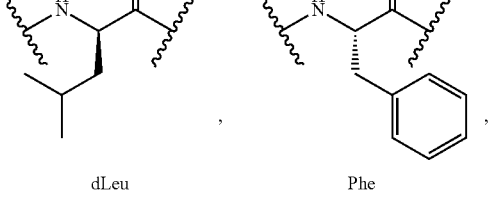
dAla ,
,

,
, dLeu
Phe

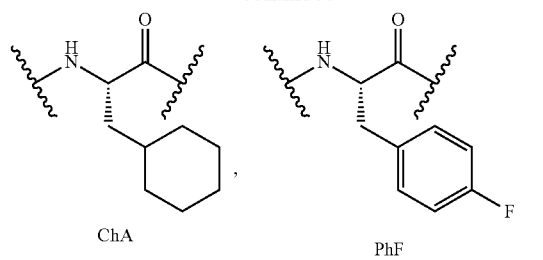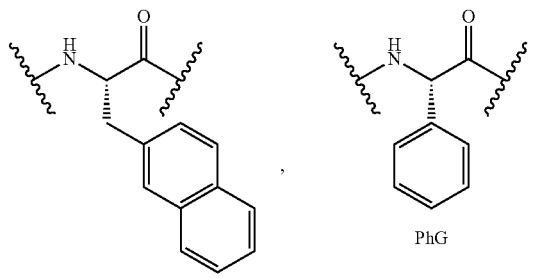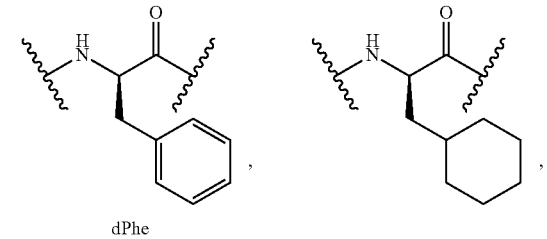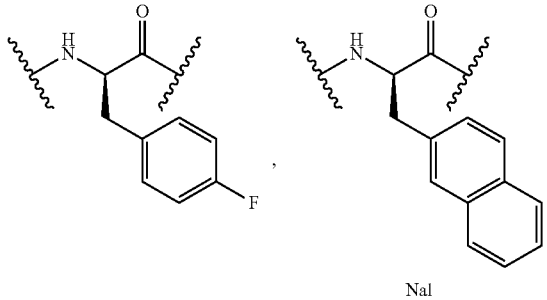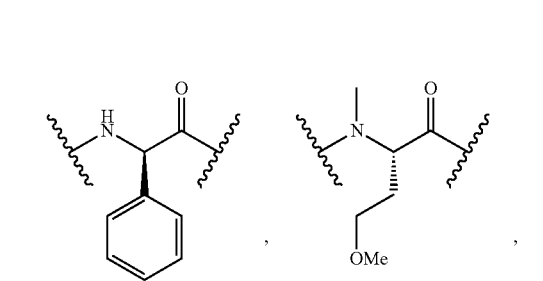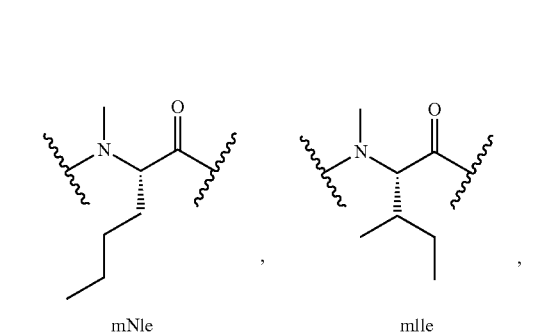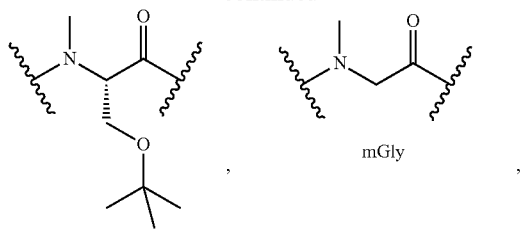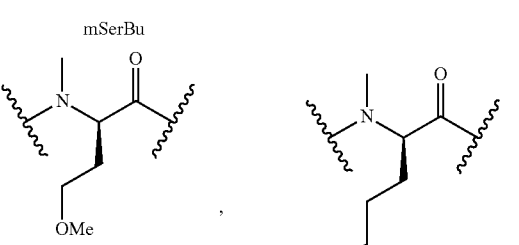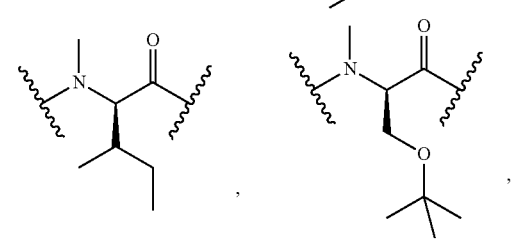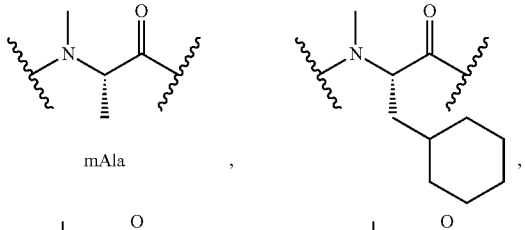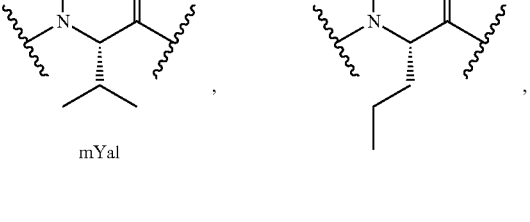

-continued

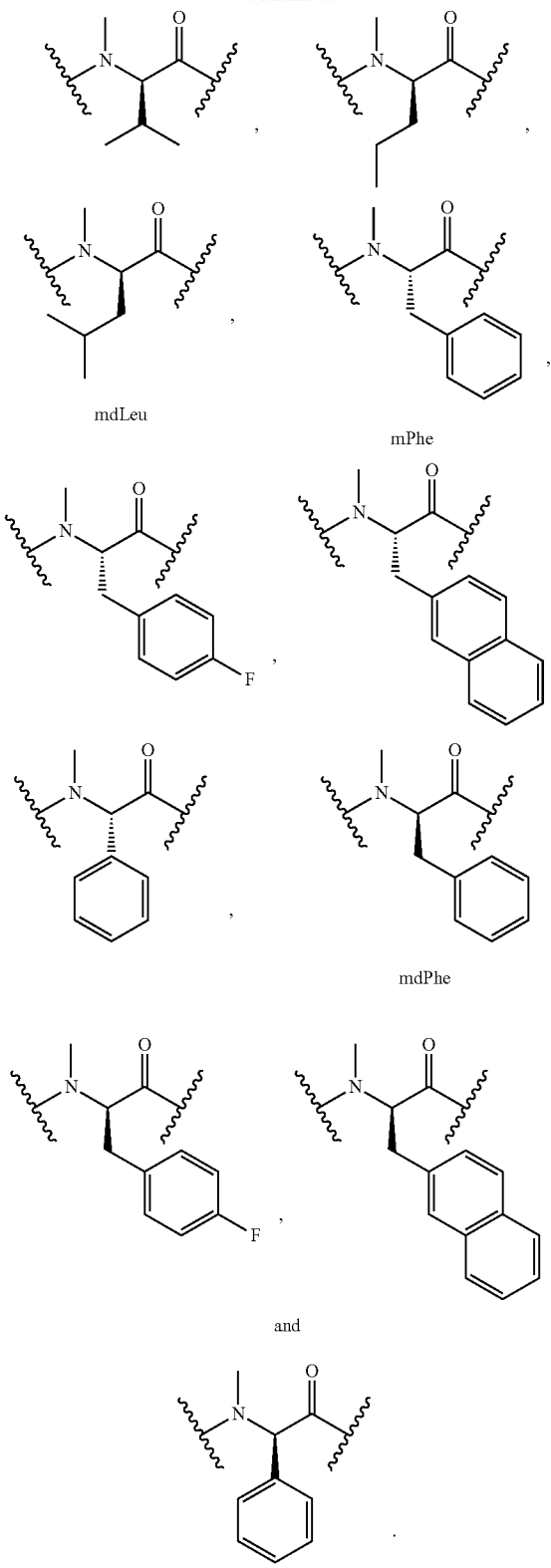

mdLeu, mPhe, mdPhe, and

2. The compound of claim 1, wherein $X_2$ is O and $L_1$ is —$CH_2$—C(O)—.

3. The compound of claim 1, wherein $X_2$ is $NR^6C(O)$ and $L_1$ is —$(CH_2)_2C(O)$—.

4. The compound according to claim 1, with the following formula

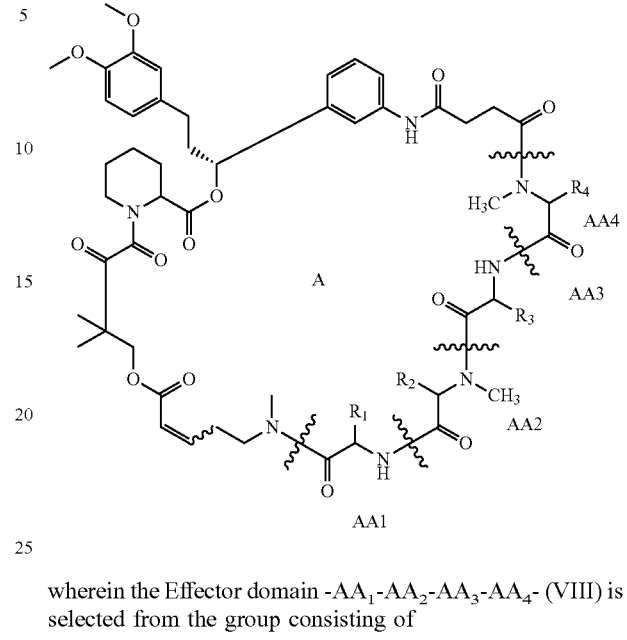

wherein the Effector domain -$AA_1$-$AA_2$-$AA_3$-$AA_4$- (VIII) is selected from the group consisting of

| Compound Name | -$AA_1$-$AA_2$-$AA_3$-$AA_4$- Sequence |
| --- | --- |
| A15-39-1 | Gly-dmPhe-Pro-mVal |
| A15-39-2 | Ala-dmPhe-Pro-mVal |
| A15-39-4 | Nva-dmPhe-Pro-mVal |
| A15-39-6 | Leu-dmPhe-Pro-mVal |
| A15-39-8 | Phe-dmPhe-Pro-mVal |
| A15-39-15 | Phg-dmPhe-Pro-mVal |
| A15-40-2 | Ala-dmPhe-Pro-mIle |
| A15-40-4 | Nva-dmPhe-Pro-mIle |
| A15-40-15 | Phg-dmPhe-Pro-mIle |
| A15-34-2 | Ala-dmPhe-Pro-mLeu. |

5. The compound according to claim 1, with the following formula

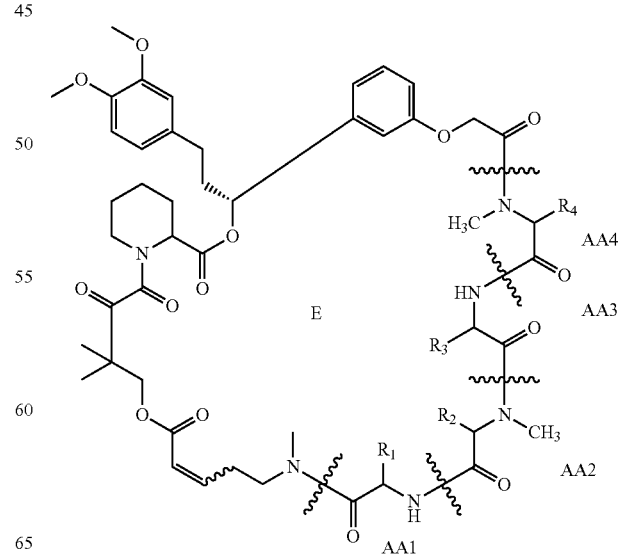

wherein the Effector domain -AA$_1$-AA$_2$-AA$_3$-AA$_4$- (VIII) is selected from the group consisting of

| Compound Name | -AA$_1$-AA$_2$-AA$_3$-AA$_4$- Sequence |
|---|---|
| E15-39-1 | Gly-dmPhe-Pro-mVal |
| E15-39-2 | Ala-dmPhe-Pro-mVal |
| E15-39-5 | HoSMe-dmPhe-Pro-mVal |
| E15-40-2 | Ala-dmPhe-Pro-mIle |
| E15-40-4 | Nva-dmPhe-Pro-mIle |
| E15-32-2 | Ala-dmPhe-Pro-mAla |
| E15-33-1 | Gly-dmPhe-Pro-mNle |
| E15-33-2 | Ala-dmPhe-Pro-mNle |
| E15-34-1 | Gly-dmPhe-Pro-mLeu |
| E15-34-2 | Ala-dmPhe-Pro-mLeu |
| E15-S-19 | Gly-dmPhe-Pro-mNva |
| E15-S-21 | Gly-dmPhe-Pro-dmAla |
| E15-S-22 | Gly-dmPhe-Pro-Ach. |

\* \* \* \* \*